(12) United States Patent
Levinson (10) Patent No.: US 6,833,000 B2
(45) Date of Patent: *Dec. 21, 2004

(54) TISSUE CUTTING AND RETRIEVAL DEVICE AND METHOD

(76) Inventor: Melvin E. Levinson, 12700 SW. 64 Ct., Pinecrest, FL (US) 33156

( * ) Notice: Subject to any disclaimer, the term of this patent is extended or adjusted under 35 U.S.C. 154(b) by 19 days.

This patent is subject to a terminal disclaimer.

(21) Appl. No.: 10/245,132

(22) Filed: Sep. 17, 2002

(65) Prior Publication Data

US 2003/0153909 A1 Aug. 14, 2003

Related U.S. Application Data

(63) Continuation-in-part of application No. 10/057,422, filed on Jan. 24, 2002, now Pat. No. 6,585,734.
(60) Provisional application No. 60/322,763, filed on Sep. 17, 2001.

(51) Int. Cl.$^7$ .............................................. A61B 17/24
(52) U.S. Cl. ........................................ 606/113; 606/47
(58) Field of Search ............................ 606/41, 47, 113, 606/127, 128

(56) References Cited

U.S. PATENT DOCUMENTS

| | | | |
|---|---|---|---|
| 4,503,855 A | * | 3/1985 | Maslanka ..................... 606/47 |
| 5,376,094 A | * | 12/1994 | Kline ......................... 606/113 |
| 5,397,320 A | | 3/1995 | Essig et al. |
| 5,997,536 A | | 12/1999 | Osswald et al. |
| 6,013,086 A | * | 1/2000 | Ouchi et al. ................. 606/113 |
| 6,152,922 A | * | 11/2000 | Ouchi ......................... 606/47 |
| 6,183,482 B1 | * | 2/2001 | Bates et al. ................. 606/127 |
| 6,585,734 B2 | * | 7/2003 | Levinson ..................... 606/47 |
| 6,660,011 B2 | * | 12/2003 | Levinson .................... 606/113 |

* cited by examiner

Primary Examiner—Michael Peffley
(74) Attorney, Agent, or Firm—McDermott Will & Emery LLP (57) ABSTRACT

A device for cutting and retrieving tissue, includes a handle, a first set of at least one wire, and a second set of at least one wire. The handle includes an elongated shaft, a tube, a first sleeve member disposed over the shaft, and a second sleeve member disposed over the shaft. The shaft defines a passageway therein. The tube connects to and extends from a distal end of the passageway, and forms a continuing channel with the passageway. The two sets of wires, attached respectively to the first sleeve member and the second sleeve member, extend through the channel to distal ends of the wires, and form loops at their distal ends. A control tip is secured to the distal end of the first set of wire. A retaining pin is secured to the control tip, extends between at least two wires of the loop of the second set of wire, allows the second set of wire to be extended from the tube and through the control tip, and prevents the second set of wire from being withdrawn from the control tip and into the tube. The retaining pin also extends the second set of wire from the tube upon the first set of wire being extended from the tube.

35 Claims, 11 Drawing Sheets

TISSUE CUTTING AND RETRIEVAL DEVICE AND METHOD

CROSS-REFERENCE TO RELATED APPLICATIONS

This application is a continuation in part of U.S. patent application Ser. No. 10/057,422, filed on Jan. 24, 2002, now U.S. Pat. No. 6,585,734 the disclosure of which is incorporated herein by reference. U.S. patent application Ser. No. 10/057,422 claims priority to provisional U.S. patent application Ser. No. 60/322,763, filed on Sep. 17, 2001.

FIELD OF THE INVENTION

This invention generally relates to a surgical instrument assembly for use in cutting and retrieving objects from internal body cavities and, more specifically, to a surgical instrument assembly for use in snare cauterization procedures. The present invention also relates to a method for cutting and retrieving objects from internal body cavities and, in a preferred form, to a method for cutting, capturing and/or retrieving polyps and other aggregates of organic tissue from a patient's internal organs via a snare cauterization procedure.

BACKGROUND OF THE INVENTION

A wire snare has been used in many different configurations and for many different medical uses. The snare, when equipped for use with cautery, has been used for polypectomies. For example, during a colonoscopy, or other endoscopic procedures, a wire loop or snare, combined with cautery, is frequently used to biopsy or excise lesions. While a wire loop or snare is very effective at cutting free a lesion, it has substantially no ability to capture and/or retrieve the excised lesion.

Typically, a second instrument is used to retrieve the excised lesion. The second instrument most often is provided in the form of a wire basket having several loops angularly offset and preferably, but not necessarily, perpendicular to each other in the case of two loops and designed to trap the excised lesion, such as a stone basket used in urology and gastroenterology. The use of two different instruments, one instrument to cut and a second instrument to retrieve, however, is inconvenient, inefficient, time consuming and can sometimes lead to the loss of the excised lesion.

What is still desired is a single instrument that can snare and retrieve a lesion. Preferably, the instrument will be simple in design and reliable in use, and will allow repeated use of a snare or a retrieval configuration, as required, by simple mechanical means.

SUMMARY OF THE INVENTION

The present invention provides a simple, but elegant solution to this problem by providing a device for selectively capturing, cutting and retrieving tissue, wherein the device includes a cutting snare, or cauterization wires, that can be incorporated into a retrieval basket configuration also including a basket snare, or basket wires, without removing the cutting snare from a patient's body. It also allows repeated use of the basket or the snare configuration, as required, by simple mechanical means.

According to one aspect of the present invention, the device includes a handle having an elongated, flexible tube extending therefrom along a central axis to a distal end, a first set of elongated, flexible wires slidingly positioned within the tube and extending along the central axis from the handle to distal ends for extending out of the distal end of the tube, a control tip secured to the distal ends of the first set of wires, the control tip having a slot, and a second set of elongated, flexible wires slidingly positioned within the tube and extending along the central axis from the handle, through the slot in the control tip, to distal ends, the second set of wires being coupled at the distal ends. A retaining pin is secured to the control tip and extends transversely through the slot of the control tip and between the second set of wires. The retaining pin allows the coupled distal ends of the second set of wires to be extended from the control tip, and prevents the coupled distal ends of the second set of wires from being withdrawn from the slot of the control tip and into the tube. In addition, the retaining pin drives the coupled distal ends of the second set of wires from the distal end of the tube upon the distal ends of the first set of wires being driven from the distal end of the tube.

According to one aspect of the present invention, the first and second sets of wires have a preset shape, preferably curving in an arc near their distal ends, so that when within the tube, the wires are substantially coaxial with the tube, but when extended from the tube, their distal ends form a loop.

According to an additional aspect of the present invention, the control tip is a discrete element that is secured to the first set of wires and the slot of the control tip is oriented such that a first reference plane formed by the loops of at least two of the wires of the first set and a second reference plane formed by the loops of at least two of the wires of the second set are angularly offset. According to a further aspect, the first reference plane is substantially perpendicular to the second reference plane.

According to still another aspect of the present invention, the first set of wires includes only two wires. According to an additional aspect, the second set of wires includes only two wires.

According to another aspect of the present invention, two single wires with distal ends bent to form loops are provided to be used to cut and retrieve tissue instead of two sets of wires. Preferably, the wire includes a front portion with an expanded distal end and a rear portion with an expanded proximal end. The distal end of the front portion and the proximal end of the rear portion are joined by a tube with crimped ends, wherein the front portion and the rear portion are relatively rotatable with each other.

According to another aspect of the present invention, the first set of wires of the device is formed by a single continuing wire folded at a distal end, instead of two wires connected to a discrete contral tip. The distal end of the continuing retrieving wire forms a "control tip", preferably an "S" or "8-like" shape structure having two apertures and one effective retaining pin portion in the middle. Two wires of the second set of wires (cutting wires) are joined at a distal end and are slidingly positioned within the tube, extending along the central axis from the handle, and wherein each wire of the set passes through one of the two apertures of the control tip. The distal end of the cutting wires is retained by the retaining pin. The "S" or "8-like" shape control tip replaces the discrete control tip of the previously described embodiment, functioning as a retaining pin for retaining the cutting wires, and also as a bottom a "basket" formed by the retrieving wires and the cutting wires, used to retrieve tissues.

According to a further aspect of the present invention, the device includes a first deployment assembly operatively connected to the first set of wires and allowing a user to selectively extend and withdraw the distal ends of the first set of wires from the distal end of the tube, and a second deployment assembly operatively connected to the second set of wires and allowing a user to selectively extend and withdraw the distal ends of the second set of wires from the distal end of the tube. According to another aspect, a latching mechanism is provided for connecting the first and second deployment assemblies. In accordance with an additional aspect, a locking mechanism is provided for preventing movement of the first deployment assembly.

According to another aspect of the present invention, the handle of the present invention includes an elongated shaft extending along a central axis, a tube connected to a distal end of the shaft, a first sleeve member disposed over the shaft and a second sleeve member disposed over the shaft. The shaft has a front portion, rear portion, and a central portion. The shaft defines an elongated slot through the central portion and an interior channel through the rear portion. The tube connects to and extends from a distal end of the interior channel and forms a elongated continuing passageway with the slot and the interior channel of the shaft for the two sets of wires to pass through. The first set of wires is attached to a first terminal lock which extends from an inner surface of the first sleeve member into the slot of the shaft. The second set of wires is attached to a second terminal lock which extends from an inner surface of the second sleeve member into the slot. Preferably, the second terminal lock defines a slot in a central portion of the second terminal lock for allowing the first set of wires to pass through. The handle also includes a first latch mechanism connected to a proximal end of the first sleeve member and the front portion of the shaft, and a second latch mechanism connected to a distal end of the first sleeve member and a proximal end of the second sleeve member.

During operation, when the device is used for cutting tissue, the first sleeve member with the first set of wires is locked to the shaft by the first latch mechanism and the second sleeve member is released and movable along the shaft. The second set of wires which is attached to the second terminal lock of the second sleeve member is moved with the second sleeve member, and the distal ends of the second set of wires are extended and withdrawn to cut tissue captured by the wires. When the device is used in retrieving excised lesion or tissue, the first latch mechanism is released, and the first sleeve member and the second sleeve member are locked together by the second latch mechanism. The first sleeve member and the second sleeve member with the two sets of wires attached are moved as a unit along the shaft and work as a retrieving tool.

According to another aspect of the present invention, the first sleeve member includes a bearing member and a ring roatatably retained on the bearing member. The ring defines a second slot adapted for engaging with a pin member extending from the second sleeve member. The slot and the pin member constitute the second latch mechanism connecting with the first sleeve member and the second sleeve member. An operator may selectively lock the first sleeve member with the second sleeve member or release the latch mechanism by rotating the ring, and as the same time keep the bearing stationary with respect to the shaft.

According to still another aspect of the present invention, the device comprises a latch mechanism which includes a hook mounted on the first sleeve member by pivot, a first pin member mounted on the shaft, and a second pin member mounted on the second sleeve member. Preferably, the hook has a substantially "W-like" shape with two arms extending from a central portion. The hook may selectively lock the first sleeve member with the shaft by engaging with the first pin member on the shaft, or lock the first sleeve member with the second sleeve member by engaging with the second pin member on the second sleeve member. The two arms of the hook are sized such that the hook may only catch one pin at a time. Each arm of the hook has a relatively small protrusion extending inwardly from the distal end of the arm, so that the hook may maintain on the pin when it engages with the pin.

The present invention also provides a method for selectively capturing, cutting and retrieving tissue in a body cavity using a device as defined above. The method includes inserting into the body cavity the distal end of the elongated, flexible tube, and manipulating the second set of wires from the handle so that distal ends of the second set extend from the distal end of the tube and capture tissue to be cut between at least two wires of the second set. A cauterizing current is then applied to the second set of wires such that the tissue is cut, and the first set of wires is manipulated from the handle so that the distal ends of the first set of wires and the control tip extend from the distal end of the tube and capture the cut tissue between the first and the second sets of wires. The distal end of the tube, together with the first and the second sets of wires and the cut and captured tissue, is subsequently withdrawn from the body cavity.

A monopolar RF electrocautery is used in one preferred embodiment. RF energy is applied to the cutting wires at proximal ends of the cutting wires from an external source. Ground conductor is appropriately positioned external to the patient.

These and other features and benefits of the presently disclosed device and method will become more apparent upon reading the following specification in combination with the accompanying drawing figures.

BRIEF DESCRIPTION OF THE DRAWINGS

Like reference characters designate identical or corresponding components and units throughout the several views.

DETAILED DESCRIPTION OF PREFERRED EMBODIMENTS

Figure 1:
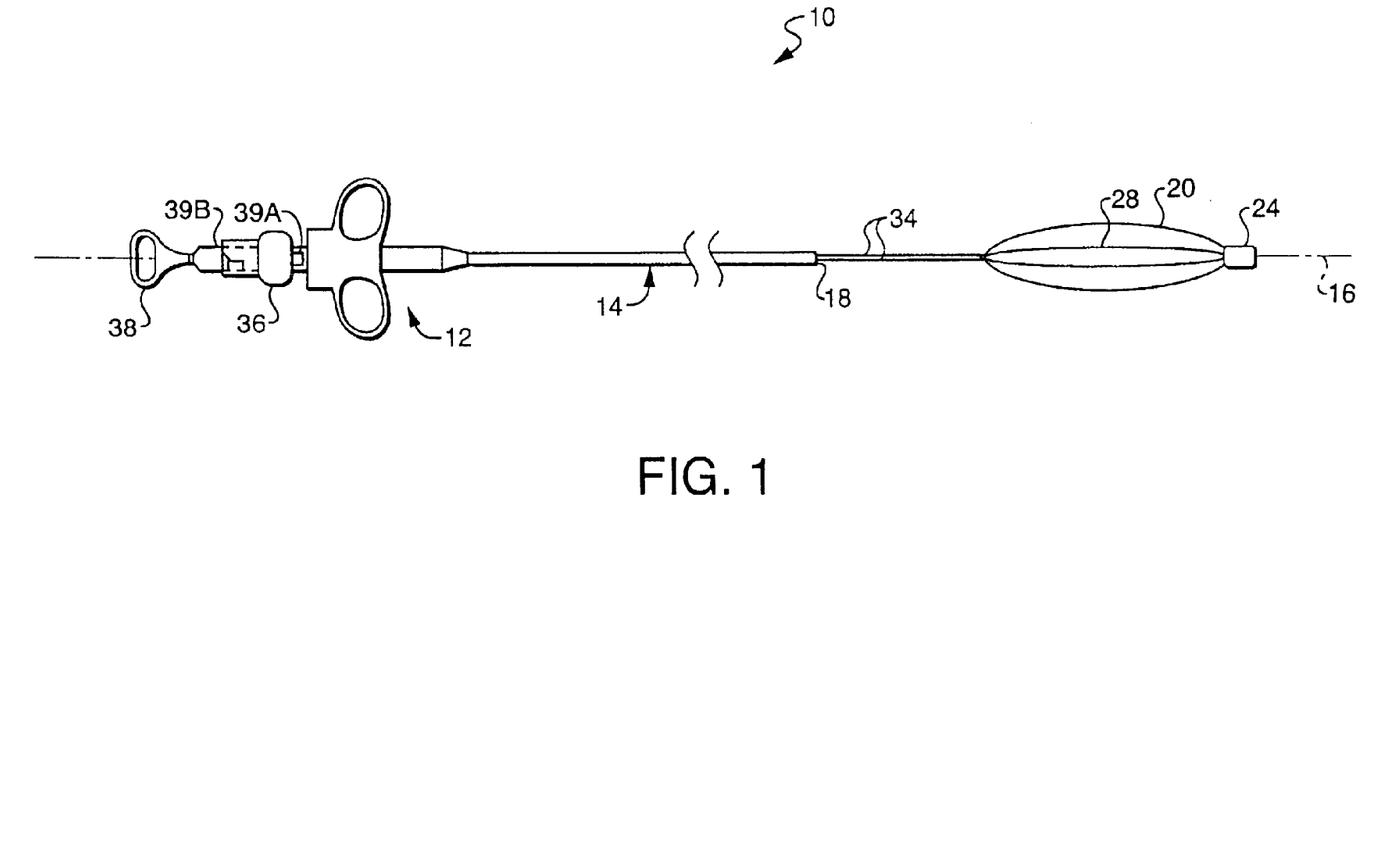
FIG. 1 is a side elevation view of an exemplary embodiment of a device constructed in accordance with the present invention for selectively capturing, cutting and retrieving tissue.

Referring first to FIG. 1, there is shown an exemplary embodiment of a device 10 constructed in accordance with the present invention for selectively capturing, cutting and retrieving tissue from within an interior cavity of a patient. The device 10 generally includes a handle 12 having an elongated, flexible tube 14 extending therefrom along a central axis 16 to a distal end 18.

Figure 2:
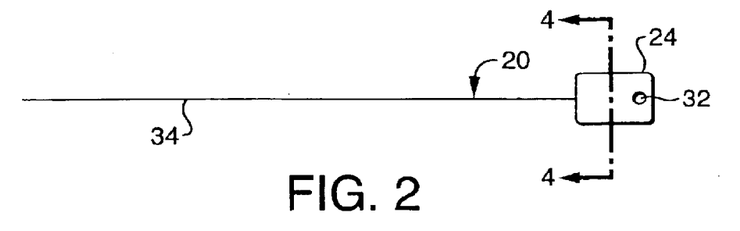
FIG. 2 is a top plan view of a first set of (or "basket") wires and a control tip of the device of FIG. 1.
Figure 3:
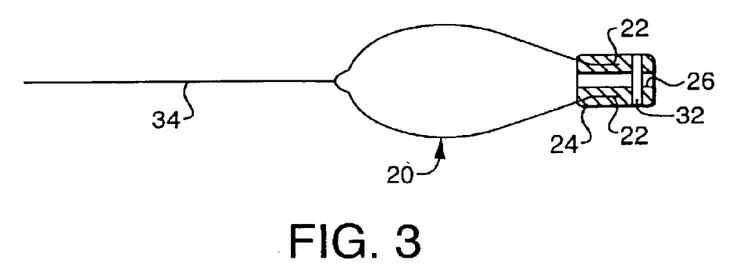
FIG. 3 is a side elevation view, partially in section, of the first set of wires and the control tip of the device of FIG. 1.
Figure 4:
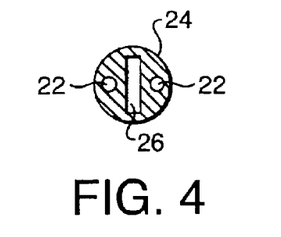
FIG. 4 is a sectional view of the first set of wires and the control tip of the device of FIG. 1, taken along line 4—4 of FIG. 2.
Figure 5:
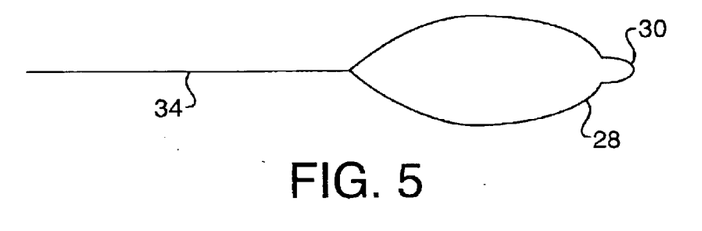
FIG. 5 is a side elevation view of a second set of (or "cauterization") wires of the device of FIG. 1.
Figure 6:
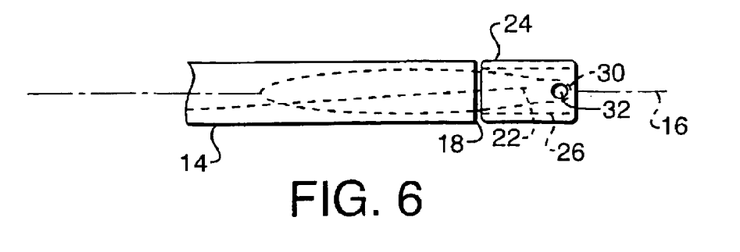
FIG. 6 is an enlarged side elevation view of the first set of wires extending out of a tube of the device of FIG. 1, the control tip positioned adjacent a distal end of the tube, and the second set of wires extending out of the tube and through the control tip.

A first set of elongated, flexible wires 20 is slidingly positioned within the tube 14 and extends along the central axis 16 from the handle 12 to distal ends 22 extending out of the distal end 18 of the tube 14. The first set of wires 20 is also shown in FIGS. 2, 3 and 6. A control tip 24 is secured to the distal ends 22 of the first set of wires 20, as also shown in FIGS. 2, 3, 4 and 6. A second set of elongated, flexible wires 28 is slidingly positioned within the tube 14 and extends along the central axis 16 from the handle 12, through a slot 26 in the control tip 24, to distal ends. The slot 26 of the control tip 24 is shown best in FIGS. 3, 4 and 6. The second set of wires 28 is coupled at the distal ends 30, as shown in FIGS. 5 and 6.

A retaining pin 32 is secured to the control tip 24 and extends through the slot 26 of the control tip 24 and between at least two wires of the second set of wires 28. The retaining pin 32, which is shown best in FIGS. 2, 3 and 6, allows the distal ends 30 of the second set of wires 28 to be extended through the control tip 24, and prevents the coupled distal ends 30 of the second set of wires 28 from being withdrawn from the slot 26 of the control tip 24 and into the tube 14. In addition, the retaining pin 32 extends the distal ends 30 of the second set of wires 28 from the distal end 18 of the tube 14 upon the distal ends 22 of the first set of wires 20 being extended from the distal end of the tube 14.

In the exemplary embodiment shown in the drawings, the first set of wires 20 includes two wires, and the second set of wires 28 includes two wires. It should be understood, however, that the first and second sets of wires 20, 28 can each be provided with more than two wires. The wires are formed of a thin spring or shape metal, which allows the wires to completely collapse and be retracted into the tube 14 and expand upon being extended from the distal end 18 of the tube 14. Preferably, each of the first and the second sets of wires 20, 28 are formed such that they each expand to an oval loop upon being extended from the distal end of the tube 14, but can be formed to expand to other shapes, such as a spiral shape. The first and the second sets of wires 20, 28 are formed from shape-memory metals such as stainless steel and nitinol, which have "memory" or the ability to retain their original shape when extended from the tube 14. The sets of wires 20, 28 can utilize hollow or solid extensions 34 from the handle 12, and can either pass side by side through the tube 14, or one extension can extend through the other extension (such as hypotube) for more accurate approximation.

The control tip 24 is secured to the first set of wires 20 and the slot 26 of the control tip 24 is oriented such that a first reference plane formed by at least two of the wires of the first set 20 and a second reference plane formed by at least two of the wires of the second set 28 are angularly offset. Preferably, the control tip 24 holds the two sets of wires 20, 28 such that the first reference plane is substantially perpendicular to the second reference plane, so that the wires form a desired "retrieval basket" when both sets of wires 20, 28 are extended as shown in FIG. 1. The tube 12, the control tip 24 and the pin 32 can each be made of stainless steel or Teflon® or other suitable material.

Referring to FIG. 1, the handle assembly 12 of the device 10 includes a first deployment assembly 36 operatively connected to the first set of wires 20 and allowing a user to selectively extend and withdraw the distal ends 22 of the first set of wires 20 from the distal end 18 of the tube 14, and a second deployment assembly 38 operatively connected to the second set of wires 28 and allowing a user to selectively extend and withdraw the distal ends 30 of the second set of wires 28 from the distal end 18 of the tube 14. The handle assembly 12 also includes a latching mechanism 39A that allows a user to latch the first and second deployment assemblies 36, 38, such that movement of one assembly causes movement of both assemblies, e.g., when the device 10 is being used as a retrieval tool. In addition, the handle assembly 12 is provided with a locking mechanism 39B that allows a user to prevent movement of the first deployment assembly 36 during operation of the second deployment assembly 38, e.g., when the device 10 is being used as a cutting tool. In this manner, the device 10 can be simply configured for cutting and retrieval without removing the device 10 from an internal body cavity of patient. Although not shown, the device 10 includes a connector for connecting the second set of wires 28 to a source of power, e.g., cauterizing current, for energizing the second set of wires 28 so that the wires cut tissue captured within the second set of wires 28.

Figure 7:
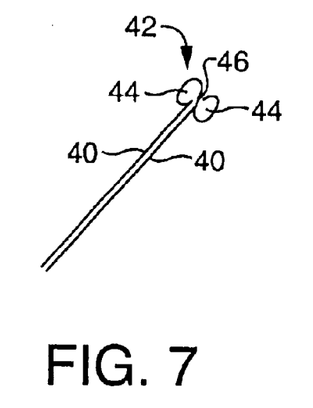
FIG. 7 is perspective view of a first set of wires of the present invention.
Figure 8A:
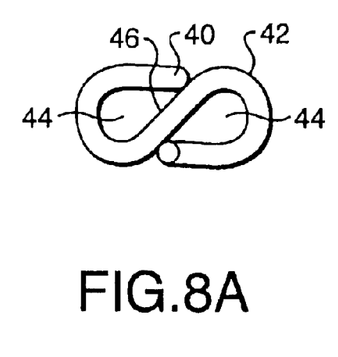
FIG. 8A is a top plan view of the first set of wires of the embodiment of FIG. 7.
Figure 8B:
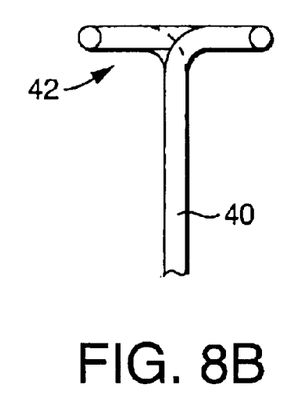
FIG. 8B is a side elevation view of the first set of wires of the embodiment of FIG. 7.

In another preferred embodiment of the present invention, as shown in FIG. 7, FIG. 8A and FIG. 8B, the first set of wires of the device 10 is formed by a single continuing retrieving wire 40 instead of two wires 20 joined at their distal ends by a discrete cap tip. The retrieving wire 40 has a distal end 42, which forms a control tip, preferably an "S" or "8-like" shape structure having two apertures 44 and one portion 46 effectively forming a retaining pin in the middle. The wires of the second set of wires 28 (cutting wires) are joined at their distal ends, and are slidingly positioned within the tube 14, extending along the central axis from the handle assembly 12. Each wire of the second set passes through the one of the two apertures 44 of the control tip. The distal end 30 of the cutting wires 28 is retained by the retaining pin 46. The "S" or "8-like" shaped control tip 42 replaces the control tip 24 of the previously described embodiment, functioning as a retaining pin for retaining cutting wires 28, and also as a bottom of retrieving wire 40 to retrieve tissues.

Figure 9:
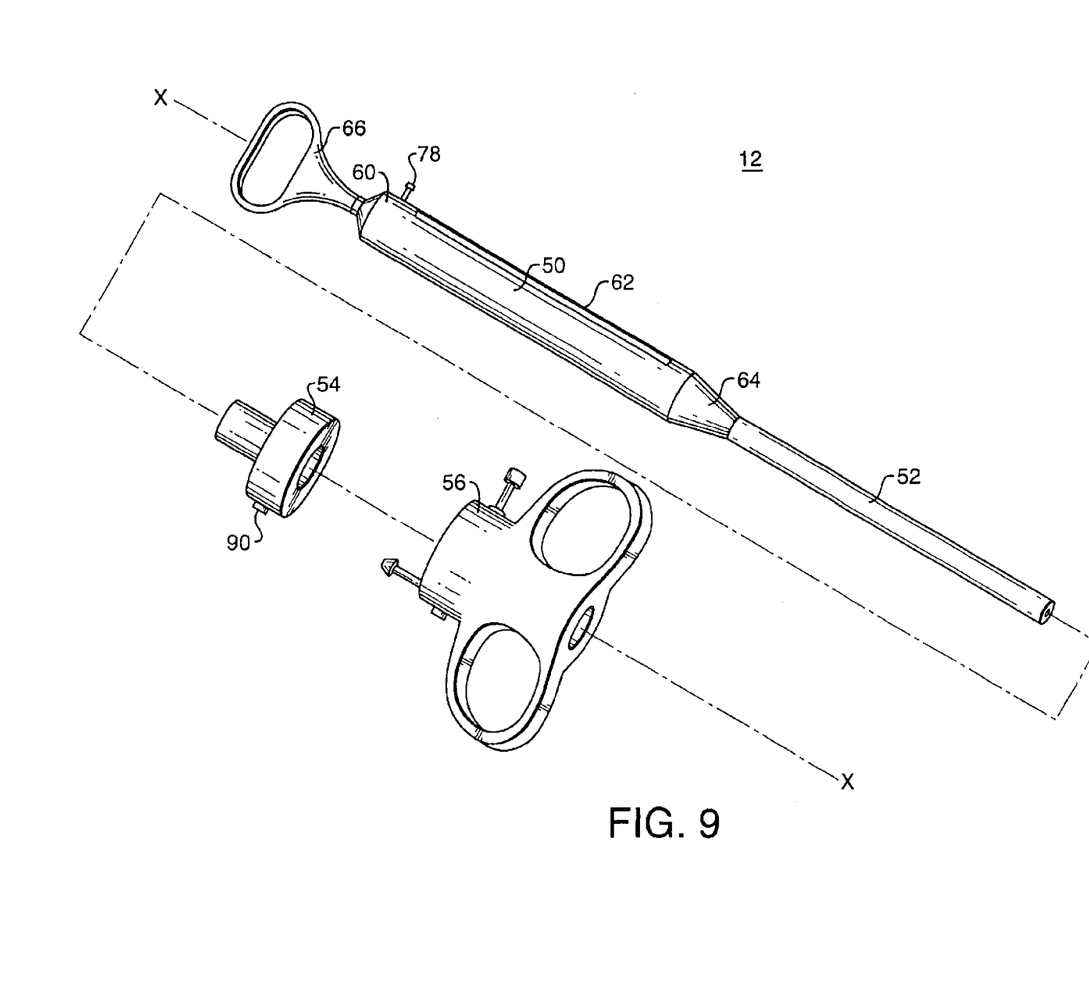
FIG. 9 is an exploded perspective view of a handle in accordance with the present invention.

FIG. 9 shows an exploded perspective view of a handle assembly in accordance to one preferred embodiment of the present invention. As shown in the drawing, the handle 12 includes an elongated shaft 50 which extends along a central axis X, an elongated tube 52, a first sleeve member 54, and a second sleeve member 56. The shaft 50 has a proximal portion 60, a central portion 62, and a distal portion 64. The proximal portion 60 forms a handle 66, which is shaped to fit human hands to hold and operate the shaft 50.

Figure 10:
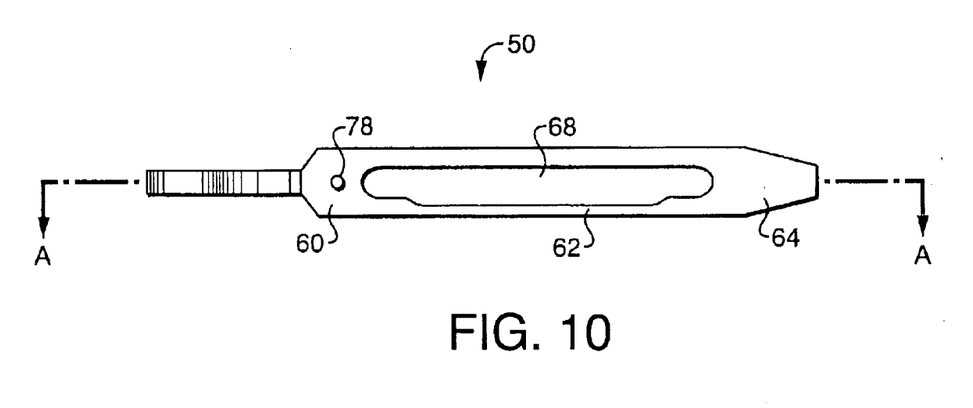
FIG. 10 is a top plan view of a shaft of the handle of FIG. 9.
Figure 11:
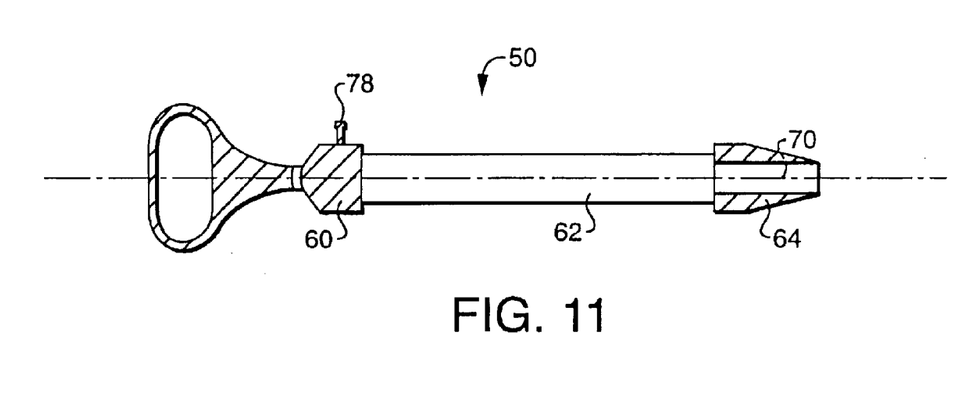
FIG. 11 is a cross-section view of the shaft of FIG. 10 taken along the line A—A in FIG. 10.

As shown in FIG. 10 and FIG. 11, the shaft 50 defines a slot 68, which extends axially through the central portion 62. The shaft 50 further defines an interior channel 70 through the distal portion 64. Referring to FIG. 9, an elongated, flexible tube 52 is connected to a distal end of the interior channel 70. The slot 68, the interior channel 70, and the tube 52 provide a continuing passageway for the wires to pass through to reach the tissues.

Figure 12:
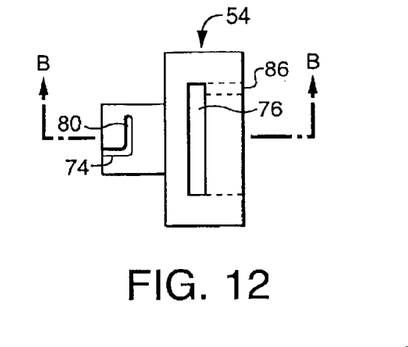
FIG. 12 is a side elevation view of a first sleeve member in accordance with the present invention.
Figure 13:
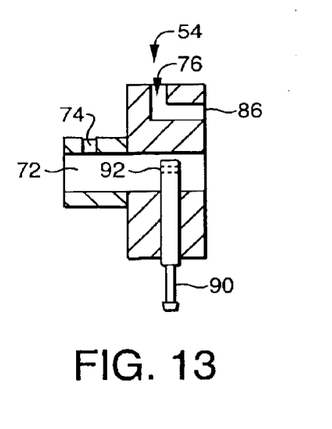
FIG. 13 is a cross section view of the first sleeve member of FIG. 12 taken along line B—B in FIG. 12.

As shown in FIG. 12 and FIG. 13, the first sleeve member 54 includes an interior channel 72, which is adapted for coupling with the shaft 50, so that the first sleeve member 54 is disposed on said shaft 50 and is rotatably and slidingly movable along the shaft 50. The first sleeve member 54 includes a first slot 74, which engages with a first pin member 78 extending from the proximal portion 60 of the shaft 50. The first slot 74 and the first pin 78 constitute a first latch mechanism connecting the shaft and the first sleeve member. When the latch is in a latched position, the first pin 78 is received by the first slot 74 into a portion 80 which is transverse to the central axis X, and therefore, the first sleeve member 54 is locked to the shaft 50, and is prevented from moving longitudinally along the shaft 50.

Figure 14:
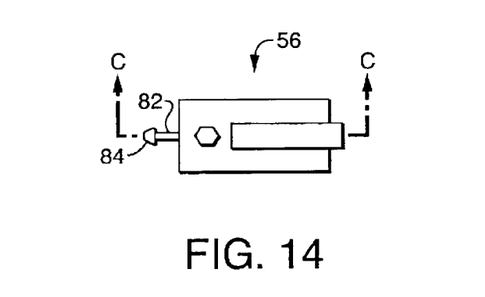
FIG. 14 is a top plan view of a second sleeve member in accordance with the present invention.
Figure 15:
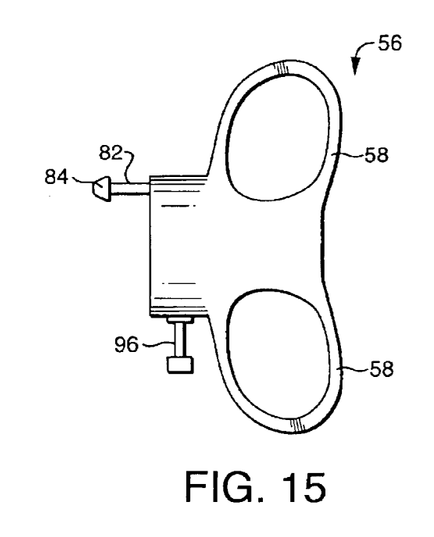
FIG. 15 is a side elevation view of the second sleeve member of FIG. 14.
Figure 16:
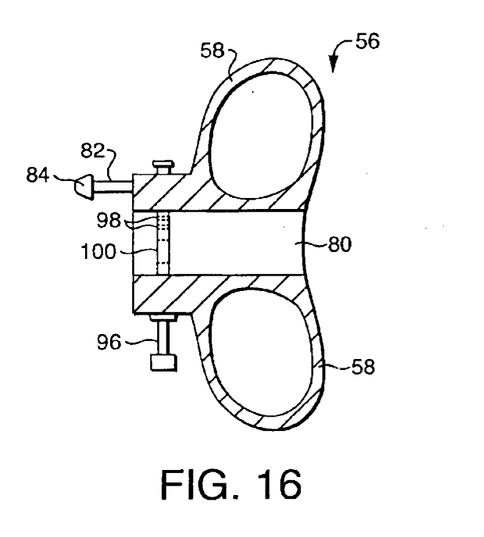
FIG. 16 is a cross section view of the second sleeve member of FIG. 14 taken along line C—C in FIG. 14.

As shown in FIG. 14, FIG. 15 and FIG. 16, in one preferred embodiment, the second sleeve member 56 has two finger holders 58 to control the sleeve member during operation. The second sleeve member also has an interior channel 80 adapted for coupling with the shaft 50. A second pin member 82 with a head 84 extends from a proximal end of the second sleeve member. The head 84 has a larger diameter than the diameter of the second pin member 82. The second pin member 82 and the head 84 are shaped to be engaged with a second slot 76 of the first sleeve member, as shown in FIG. 13. The second pin 82 and the second slot 76 constitute a second latch mechanism, which connects the first sleeve member 54 and the second sleeve member 56. In operation, the head 84 of the second pin member 82 is inserted into the second slot 76 from an opening 86 of the slot 76. When the first sleeve member 54 and the second sleeve member 56 are rotated with respect to each other about the axis X, the head 84 is moved to a part inside the slot where the opening 86 narrows down thus retains the head 84 and the pin member 82 from moving longitudinally along the axis X. When the first latch mechanism is in a released position and the second latch mechanism is in a latched position, the first sleeve 54 and the second sleeve 56 are locked together and are movable as a unit along the shaft 50.

As shown in FIG. 13, the handle 12 also includes a first terminal lock 90, which extends radially through the side wall of the first sleeve member 54 into the slot 68 of the shaft 50. In one preferred embodiment, the proximal ends of the first set of wires 20 is inserted into and locked in an aperture 92 of the terminal lock 90. As shown in FIG. 15 and FIG. 16, a second terminal lock 96 extends radially through the second sleeve member 56. In a preferred embodiment, the second terminal lock 96 has two apertures 98 for attaching and locking the terminals of the second set of wires 28. The terminal lock 96 includes a slot 100 extending through a central portion of the terminal lock 96. The slot 100 is aligned with the first terminal lock 90 along the central axis X, so that the first set of wires 20 which is attached to the first terminal lock 90 passes through the slot 100.

During operation, when the device is used in cutting tissue, the first sleeve member 54 with the first set of wires 20 is locked to the shaft 50 by the first latch mechanism and the second sleeve member 56 is released and movable along the shaft 50. The second set of wires 28 which is attached to the second terminal lock 96 of the second sleeve member 56 is moved with the second sleeve member 56, and the distal ends of the second set of wires are extended and withdrawn to cut tissue captured by the wires. When the device is used in retrieving excised lesion or tissue, the first sleeve member 54 is released and movable along the shaft 50, and the second sleeve member 56 is locked to the first sleeve member 54 by the second latch mechanism. The first sleeve member 54 and the second sleeve member 56 with the two sets of wires 20 and 28 attached are moved as a unit along the shaft and work as a retrieving basket.

Figure 17:
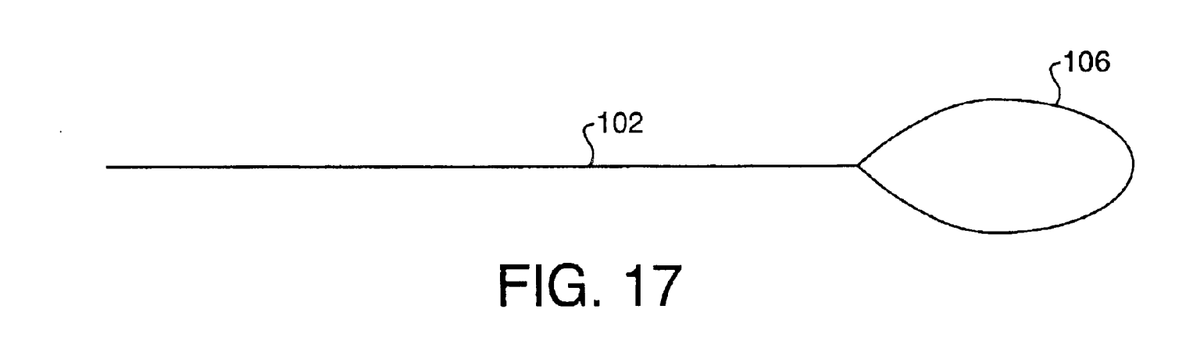
FIG. 17 shows a single wire of a first set with a distal end bent to form a loop in accordance with one preferred embodiment of the present invention.
Figure 18:
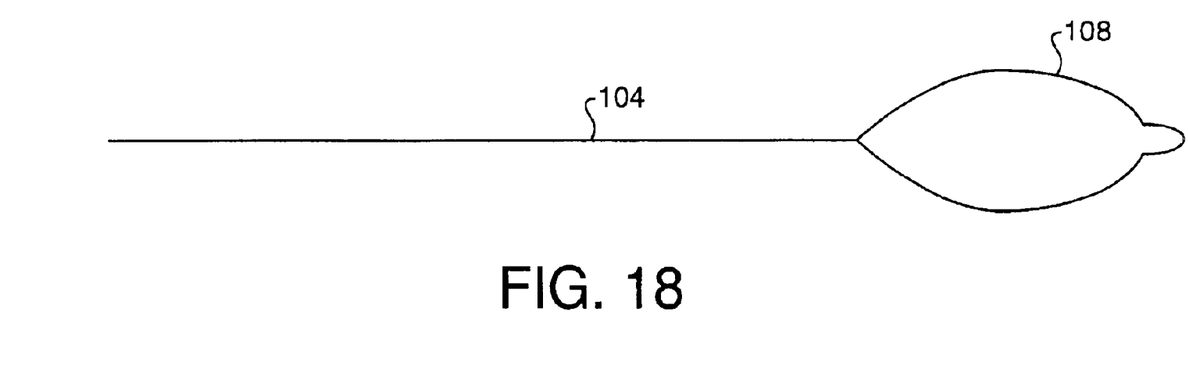
FIG. 18 shows a single wire of a second set with a distal end bent to form a loop in accordance with one preferred embodiment of the preferred invention.

Referring to FIG. 17 and FIG. 18, in one preferred embodiment, the device includes two single wires 102 and 104 attached to the first sleeve member 54 and the second sleeve member 56 instead of two sets of wires. Both of the wires 102 and 104 bend at distal ends to form loops 106 and 108. The loop 108 of the second wire 104 functions as a cutting device and the loop 106 coupled with a control tip and/or with the loop 108 function to retrieve excised lesions.

Figure 19:
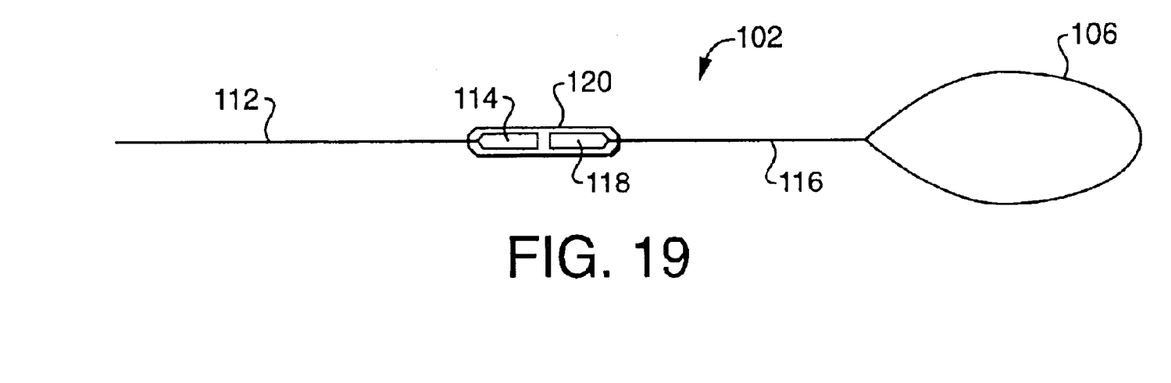
FIG. 19 shows a wire of a first set having two portions rotatably joined by a tube in accordance with one preferred embodiment of the present invention.
Figure 20:
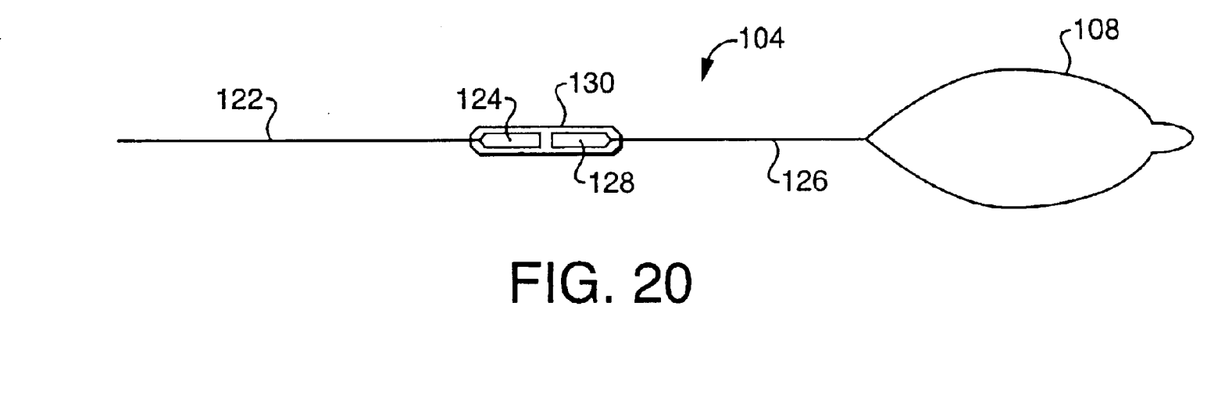
FIG. 20 shows a wire of a second set having two portions rotatably joined by a tube in accordance with one preferred embodiment of the present invention.

FIGS. 19 and 20 show another alternative embodiment of the present invention, in which the retrieving wire 102 includes a front portion 112 having an expanded distal end 114 and a rear portion 116 having an expanded proximal end 118. The expanded distal end 114 and the expanded proximal end 118 may be shaped substantially rectangular or oval, and are joined by a tube 120 with crimped ends. The tube 120 is size to allow the distal end 114 and the proximal 118 rotate relatively to each other within the tube. The cutting wire 104 also includes a front portion 122 and a rear portion 126, which are rotatably joined at an expanded distal end 124 of the front portion and an expanded proximal end 128 of the rear portion by a tube 130.

Figure 21:
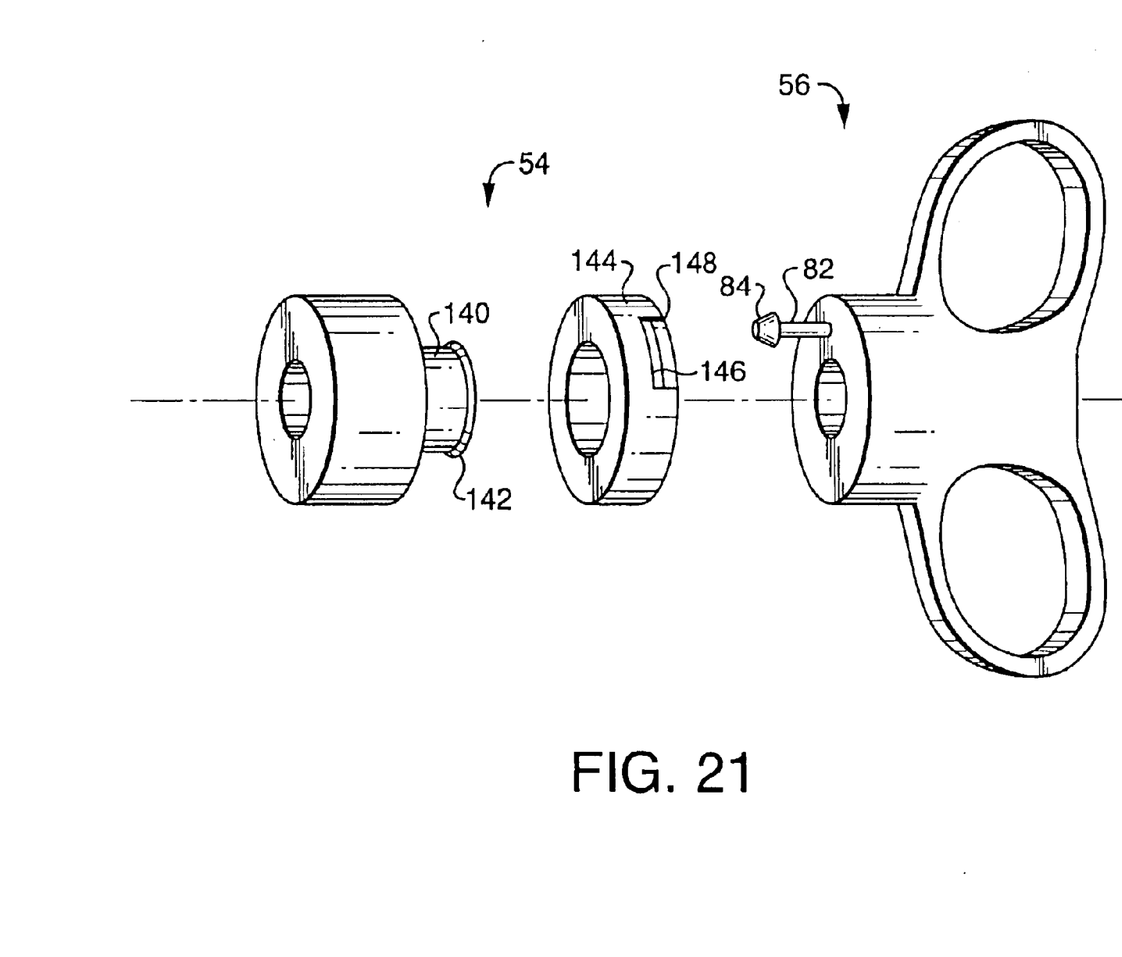
FIG. 21 is a perspective view of a first sleeve member and a second sleeve member in accordance with one preferred embodiment of the present invention.

FIG. 21 shows an alternative preferred form of the first sleeve member 54, in which the first sleeve member includes a bearing 140 with detent ends 142 and a ring 144 rotatably coupled on the bearing 140. The inner diameter of the ring 144 is sized to receive the bearing 140 and to be retained by the detent ends 142 of the bearing. The ring 144 defines a slot 146 with an opening 148. The slot 146 and the opening 148 are adapted to engage with the second pin member 82 and the pin head 84 of the second sleeve member 56. In operation, the second pin 82 is inserted into the slot 146 from the opening 148. When the first sleeve member 54 and the second sleeve member 56 are rotated with respect to each other about the axis X, the pin 82 is moved to a part inside the slot where the opening 148 narrows down, thus the head 84, with a larger diameter than that part of the opening 148, is retained from moving longitudinally along the axis X, so that the second sleeve member 56 is locked to the first sleeve member 54. When the first latch mechanism is in a released position and the second latch mechanism is in a latched position, the first sleeve 54 and the second sleeve 56 are locked together and are movable as a unit along the shaft 50.

Figure 22:
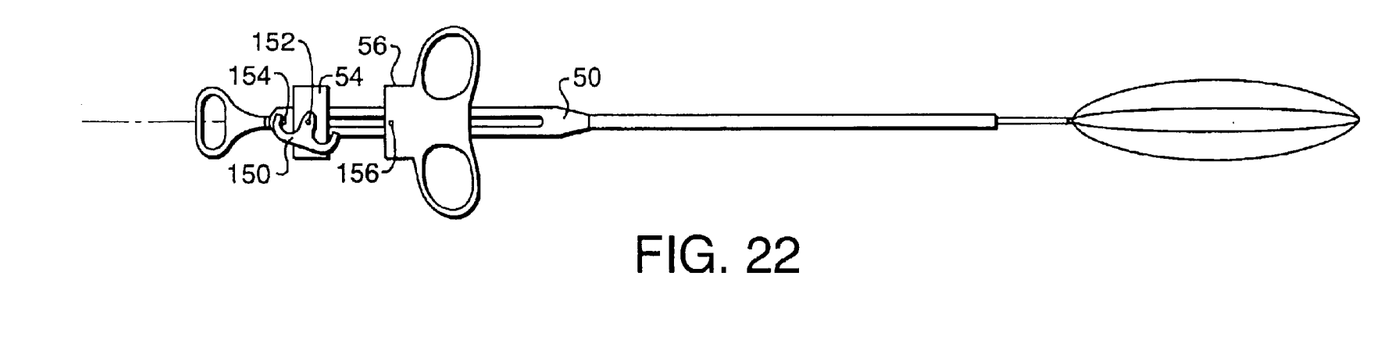
FIG. 22 shows a latch mechanism in a first position in which a first sleeve member is locked to a shaft by the latch mechanism.
Figure 23:
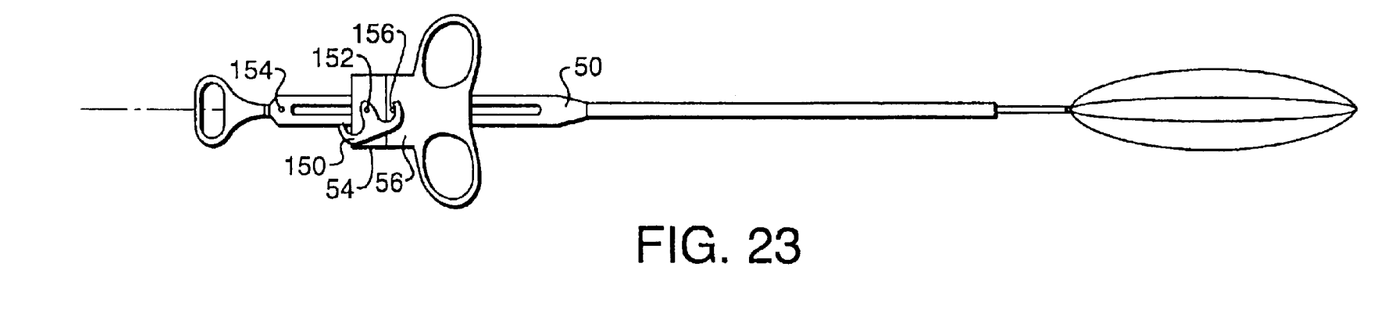
FIG. 23 shows the latch mechanism of FIG. 22 in a second position in which the first sleeve member is locked to the second sleeve member by the latch mechanism.

In another preferred embodiment of the present invention, the device comprises a latch mechanism connected with the shaft, the first sleeve member, and the second sleeve member. The latch may selectively lock the first sleeve member to the shaft and to the second sleeve member. As show in FIGS. 22 and 23, the latch mechanism comprising a hook 150 mounted on the first sleeve member 54 by a pivot 152, a first pin 154 mounted on the shaft 50, and a second pin 156 mounted on the second sleeve member 56. Preferably, the hook 150 has a substantially W-like shape with two arms extending from a central portion. The two arms of the hook are sized such that the hook may only catch one pin at a time. Each arm of the hook has a relatively small protrusion extending inwardly from the distal end of the arm, so that the hook may maintain on the pin when it engages with the pin. In a first position, as shown in FIG. 22, the hook 150 is engaged with the first pin 154 on the shaft, and thereby locks the first sleeve member 54 to the shaft 50 to prevent the first sleeve member from moving longitudinally along the shaft 50. In a second position, as shown in FIG. 23, the hook, by engaging with the second pin 156 on the second sleeve member 56, locks the first sleeve member to the second sleeve member, thereby the first sleeve member and the second sleeve member may be moved as a unit along the shaft. Through the operation of the first and second sleeve members, the cutting wires and the retrieving wires attached to the first and second sleeve members are manipulated from the handle.

Figure 24:
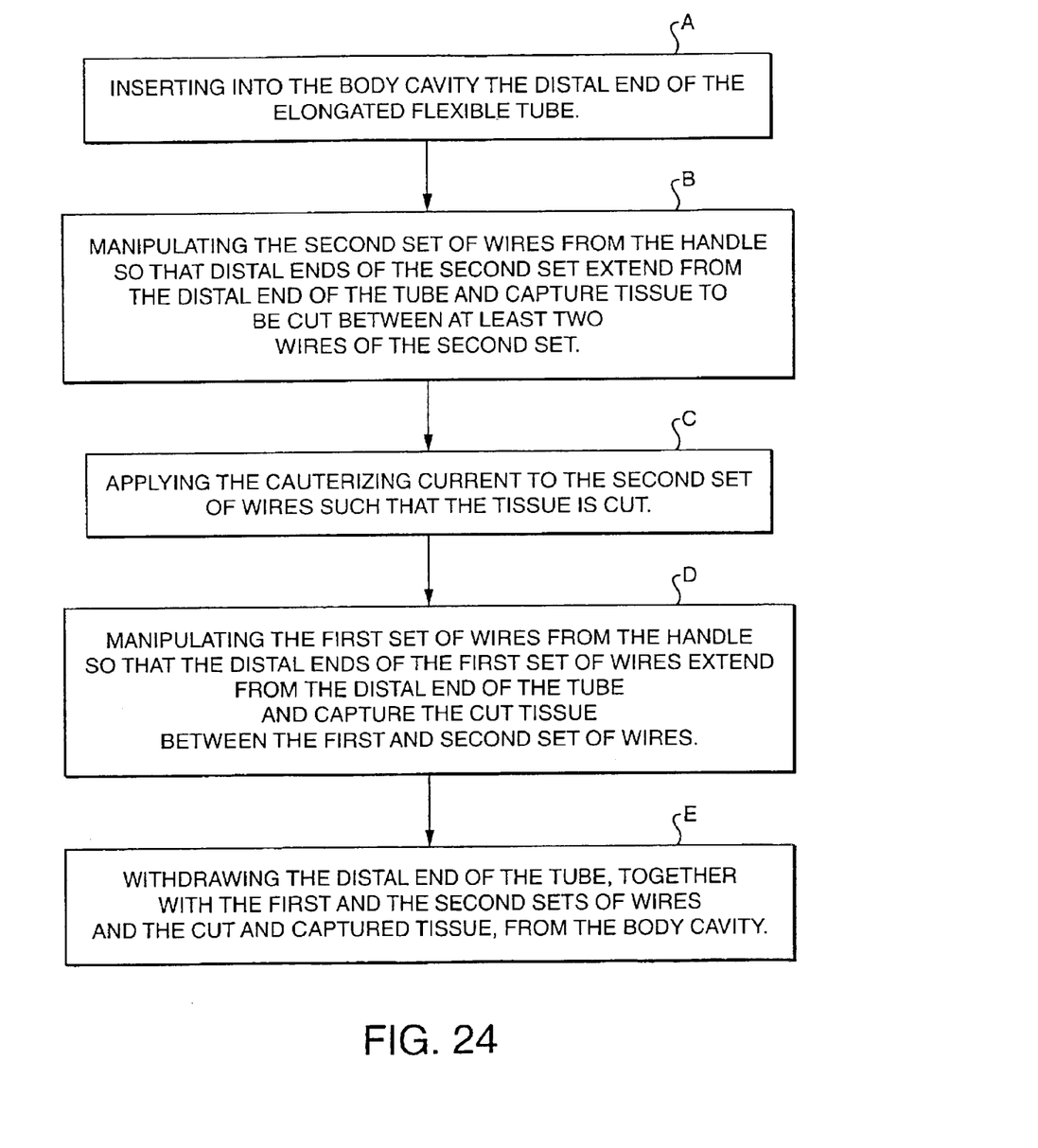
FIG. 24 is a flow chart illustrating a method according to the present invention for selectively capturing, cutting and retrieving tissue.

Referring to FIG. 24, the present invention also provides a method for selectively capturing, cutting and retrieving tissue in a body cavity using the device of the present invention. The method includes inserting into the body cavity the distal end of the elongated, flexible tube, as shown at "A", and manipulating the second set of wires from the handle assembly so that distal ends of the second set of wires extend from the distal end of the tube and capture tissue to be cut between at least two wires of the second set, as shown at "B". A cauterizing current is then applied to the second set of wires such that the tissue is cut, as shown at "C", and the first set of wires, and the control tip of the first set of wires are manipulated from the handle so that the distal ends of the first set of wires extends from the distal end of the tube and capture the cut tissue between the first and the second sets of wires, as shown at "D". The distal end of the tube, together with the first and the second sets of wires and the cut and captured tissue, is subsequently withdrawn from the body cavity, as shown at "E".

A monopolar RF electrocautery is used in one preferred embodiment. RF energy is applied to the cutting wires at proximal ends of the cutting wires from an external source. Ground conductor is appropriately positioned external to the patient.

The present invention, accordingly, provides a device and a method which allows a single instrument to function as a tissue cutting snare and a basket retriever. By replacing two or more existing instruments with a simply manufactured and easily utilized device, the present invention beneficially provides a useful, new and improved device and method for endoscopically cutting and retrieving tissue.

Modifications to the above-described exemplary embodiment of the presently disclosed invention may become apparent to those skilled in the art. The scope of the invention is therefore intended to be limited solely by the scope of the appended claims.

What is claimed is:

1. A device for selectively capturing, cutting and retrieving tissue, comprising:
  A) a handle having an elongated, flexible tube extending therefrom along a central axis to a distal end, said tube having a diameter D at its distal end;
  B) a first set of at least one elongated, flexible wire slidingly positioned within the tube and extending along the central axis from the handle to a distal end for extending out of the distal end of the tube, wherein said distal end include a control tip portion extending a distance larger than D in a direction transverse to said central axis, said control tip portion defining two apertures separated by a retaining portion,
  C) a second set of at least one elongated, flexible wire slidingly positioned within the tube and extending along the central axis from the handle to a distal end, wherein the second set of wire passes on opposite sides of said retaining portion and through an associated one of said apertures of said control tip portion,
  wherein said distal ends of said first set of wire and said second set of wire are each adapted for selective positioning along said central axis between points adjacent to said distal end of said tube and points distal therefrom.

2. A device according to claim 1, wherein said selective positioning of said first set of wire and said selective positioning of said second set of wire are independently controllable, with said distal end of said second set of wire being farther from said distal end of said tube than said distal end of said first set of wire.

3. A device according to claim 1, wherein the first set of wire and said control tip portion are formed from a single wire.

4. A device according to claim 1, wherein the second set of wire is formed from a single wire.

5. A device according to claim 1, wherein the second set of wire is made of a material adapted for carrying a cauterizing energy.

6. A device according to claim 1, further comprising:
  D) a first deployment assembly operatively connected to the first set of wire and allowing a user to selectively extend and withdraw the distal end of the first set of wire from the handle; and
  E) a second deployment assembly operatively connected to the second set of wire and allowing a user to selectively extend and withdraw the distal end of the second set of wire from the handle.

7. A device according to claim 1 further comprising a latching mechanism for connecting the first and second deployment assemblies.

8. A device according to claim 1 further comprising a locking mechanism for preventing movement of the first deployment assembly.

9. A device for selectively capturing, cutting and retrieving tissue, comprising:

A) a handle comprising:
  a) an elongated shaft extending along a central axis, said shaft defining a longitudinal passageway therein along the central axis;
  b) an elongated, flexible tube connected to and extending from a distal end of the passageway of the shaft along the central axis to a distal end of said tube;
  c) a first sleeve member disposed over said shaft and being slidingly movable on said shaft;
  d) a second sleeve member disposed over said shaft and being slidingly movable on said shaft; and
  e) a latch mechanism coupled to said first sleeve member, said shaft, and said second sleeve member, for selectively latching said first sleeve member to said shaft and said second sleeve member;
B) a first set of at least one elongated, flexible wire attached to said first sleeve member, said first set of wire extending through the passageway of said shaft and the flexible tube to a distal end for extending out of the distal end of the tube, said first set of wire forming a loop at the distal end of said first set of wire;
C) a second set of at least one elongated, flexible wire attached to said second sleeve member, said second set of wire extending through the passageway of said shaft and the flexible tube to a distal end for extending out of the distal end of the tube, said second set of wire forming a loop at the distal end of said second set of wire;
D) a control tip at the distal end of the first set of wire and including a transverse portion extending beyond the distal end of the tube in a direction transverse to the central axis, the transverse portion being adapted for interfering engagement with the distal end of said tube, thereby preventing the distal end of said first set of wire from being wholly drawn into said tube, and
wherein said control tip includes two apertures separated by a retaining portion, wherein said second set of wire passes on opposite sides of said retaining portion and through an associated one of said apertures, and wherein said retaining portion is adapted for interfering engagement with the loop of said second set of wire, thereby maintaining said distal end of said second set of wire farther from said distal end of said tube than said control tip.

10. A device according to claim 9, wherein said first set of at least one elongated, flexible wire includes a single wire having the distal end bent to form the loop.

11. A device according to claim 9, wherein said second set of at least one elongated, flexible wire includes a single wire having the distal end bent to form the loop.

12. A device according to claim 9, wherein said first set of at least one elongated, flexible wire includes a front portion having an expanded distal end, and a rear portion having an expanded proximal end, said expanded distal end of the front portion and said expanded proximal end being relatively rotatably joined by a tube.

13. A device according to claim 9, wherein said second set of at.least one elongated, flexible wire includes a front portion having an expanded distal end, and a rear portion having an expanded proximal end, said expanded distal end of the front portion and said expanded proximal end being relatively rotatably joined by a tube.

14. A device according to claim 9, wherein said latch mechanism comprising a hook pivotally mounted to the first sleeve member, a first pin extending from said shaft, and a second pin extending from said second sleeve member, and wherein said hook is adapted for selectively capturing said first pin and said second pin, and thereby selectively lock said first sleeve member with said shaft and said second sleeve member.

15. A device according to claim 14, wherein said hook has a substantially W shape.

16. A device according to claim 9, wherein said passageway of said shaft includes a slot defined through a central portion of said shaft and an interior channel defined through a rear portion of said shaft.

17. A device according to claim 9, wherein the wires have shape memory such that each of the first and the second sets of wires expand upon being extended from the distal end of the tube.

18. A device according to claim 9, wherein said first set of wire and said control tip are formed from a single wire, said control tip having a substantially S shape defining two apertures, and wherein the wire of said second set passes through each respective one of said apertures.

19. A device according to claim 9, wherein said second set of wire is made of a material adapted for carrying a cauterizing energy.

20. A device according to claim 9, wherein said first sleeve member further comprising a first terminal lock extending radially inwardly from an inner surface of said first sleeve member into said longitudinal passageway of said shaft, wherein said first set of wire attached to said first terminal lock.

21. A device according to claim 9, wherein said second sleeve member further comprising a second terminal lock extending radially inwardly from an inner surface of said second sleeve member into said longitudinal passageway of said shaft, wherein said second set of wire attached to said second terminal lock.

22. A device for selectively capturing, cutting and retrieving tissue, comprising:
  A) a handle comprising:
    a) an elongated shaft extending along a central axis, said shaft defining a longitudinal passageway therein along the central axis;
    b) an elongated, flexible tube connected to and extending from a distal end of the passageway of the shaft along the central axis to a distal end of said tube;
    c) a first sleeve member disposed over said shaft and being slidingly movable on said shaft;
    d) a second sleeve member disposed over said shaft and being slidingly movable on said shaft;
    e) a first latch mechanism coupled to said shaft and said first sleeve member for latching said first sleeve member to said shaft; and
    f) a second latch mechanism coupled to said first sleeve member and said second sleeve member for latching said second sleeve member to said first sleeve member;
  B) a first set of at least one elongated, flexible wire attached to said first sleeve member, said first set of wire extending through the passageway of said shaft and the flexible tube to a distal end for extending out of the distal end of the tube, said first set of wire forming a loop at the distal end of said first set of wire;
  C) a second set of at least one elongated, flexible wire attached to said second sleeve member, said second set of wire extending through the passageway of said shaft and the flexible tube to a distal end for extending out of the distal end of the tube, said second set of wire forming a loop at the distal end of said second set of wire;
  D) a control tip at the distal end of the first set of wire and including a transverse portion extending beyond the distal end of the tube in a direction transverse to the central axis, the transverse portion being adapted for interfering engagement with the distal end of said tube, thereby preventing the distal end of said first set of wire from being wholly drawn into said tube, and wherein said control tip includes two apertures separated by a retaining portion, wherein said second set of wire passes on opposite sides of said retaining portion and through an associated one of said apertures, and wherein said retaining portion is adapted for interfering engagement of the loop of said second set of wire, thereby maintaining said distal end of said second set of wire farther from said distal end of said tube than said control tip.

23. A device according to claim 22, wherein the first latch mechanism includes a first pin extending radially outwardly from the shaft and a first slot defined in the first sleeve member, and wherein the first slot defined in the first sleeve member is adapted for engaging with the first pin on the shaft for latching the first sleeve member to the shaft.

24. A device according to claim 22, wherein the second latch mechanism. includes a second pin extending axially from the second sleeve member towards the first sleeve member and a second slot defined in said first sleeve member, and wherein the second slot defined in the first sleeve member is adapted for engaging with the second pin for latching the second sleeve member to the first sleeve member.

25. A device according to claim 24, wherein the first sleeve member comprises a bearing and a ring rotataly retained on said bearing, and wherein said second slot is defined on said ring.

26. A device according to claim 22, wherein said first set of at least one elongated, flexible wire includes a single wire having the distal end bent to form the loop.

27. A device according to claim 22, wherein said second set of at least one elongated, flexible wire includes a single wire having the distal end bent to form the loop.

28. A device according to claim 22, wherein said first set of at least one elongated, flexible wire includes a front portion having an expanded distal end, and a rear portion having an expanded proximal end, said expanded distal end of the front portion and said expanded proximal end of the rear portion being relatively rotatably joined by a tube.

29. A device according to claim 22, wherein said second set of at least one elongated, flexible wire includes a front portion having an expanded distal end, and a rear portion having an expanded proximal end, said expanded distal end of the front portion and said expanded proximal end of the rear portion being relatively rotatably joined by a tube.

30. A device according to claim 22, wherein said passageway of said shaft includes a slot defined through a central portion of said shaft and a interior channel defined through a rear portion of said shaft.

31. A device according to claim 22, wherein the wires have shape memory such that each of the first and the second sets of wires expand upon being extended from the distal end of the tube.

32. A device according to claim 22, wherein said first set of wire and said control tip are formed from a single wire, said control tip having a substantially S shape defining two apertures, and wherein the wire of said second set passes through each respective one of said apertures.

33. A device according to claim 22, wherein said second set of wire is made of a material adapted for carrying a cauterizing energy.

34. A device according to claim 22, wherein said first sleeve member further comprising a first terminal lock extending radially inwardly from an inner surface of said first sleeve member into said longitudinal passageway of said shaft, wherein said first set of wire attached to said first terminal lock.

35. A device according to claim 22, wherein said second sleeve member further comprising a second terminal lock extending radially inwardly from an inner surface of said second sleeve member into said longitudinal passageway of said shaft, wherein said second set of wire attached to said second terminal lock.

* * * * *